(12) United States Patent
Marino et al.

(10) Patent No.: US 8,721,536 B2
(45) Date of Patent: May 13, 2014

(54) ARCUATE SURGICAL GUIDANCE SYSTEM AND METHODS

(75) Inventors: James F. Marino, La Jolla, CA (US); Jamil Elbanna, San Diego, CA (US)

(73) Assignee: Trinity Orthopedics, LLC, San Diego, CA (US)

( * ) Notice: Subject to any disclaimer, the term of this patent is extended or adjusted under 35 U.S.C. 154(b) by 584 days.

(21) Appl. No.: 12/844,757

(22) Filed: Jul. 27, 2010

(65) Prior Publication Data

US 2011/0028791 A1    Feb. 3, 2011

Related U.S. Application Data

(60) Provisional application No. 61/229,179, filed on Jul. 28, 2009.

(51) Int. Cl.
    *A61B 1/32*    (2006.01)
(52) U.S. Cl.
    USPC .......................................... 600/203; 600/208
(58) Field of Classification Search
    USPC ......... 600/203–204; 606/129–130; 623/17.11
    See application file for complete search history.

(56) References Cited

U.S. PATENT DOCUMENTS

| | | | |
|---|---|---|---|
| 3,262,452 A * | 7/1966 | Hardy et al. .................. 606/130 |
| 4,638,798 A | 1/1987 | Shelden et al. | |
| 4,723,544 A | 2/1988 | Moore et al. | |
| 4,805,615 A * | 2/1989 | Carol .......................... 606/130 |
| 4,955,891 A | 9/1990 | Carol | |
| 5,330,485 A | 7/1994 | Clayman et al. | |
| 5,474,564 A | 12/1995 | Clayman et al. | |
| 5,575,798 A | 11/1996 | Koutrouvelis | |
| 5,603,689 A * | 2/1997 | Lucini ......................... 600/201 |
| 5,649,936 A * | 7/1997 | Real ............................ 606/130 |
| 5,716,326 A * | 2/1998 | Dannan ........................ 600/204 |
| 5,776,143 A * | 7/1998 | Adams ......................... 606/130 |
| 5,788,713 A | 8/1998 | Dubach et al. | |
| 5,807,243 A * | 9/1998 | Vierra et al. .................. 600/204 |
| 5,820,555 A * | 10/1998 | Watkins et al. ............... 600/204 |
| 5,976,156 A * | 11/1999 | Taylor et al. .................. 606/130 |
| 6,152,596 A * | 11/2000 | Fraden .......................... 374/158 |
| 6,264,604 B1 * | 7/2001 | Kieturakis et al. ............ 600/207 |
| 6,482,151 B1 * | 11/2002 | Vierra et al. .................. 600/204 |
| 6,949,105 B2 * | 9/2005 | Bryan et al. .................. 606/130 |
| 7,204,840 B2 * | 4/2007 | Skakoon et al. ............. 606/129 |
| 7,306,603 B2 | 12/2007 | Boehm, Jr. et al. | |
| 7,313,430 B2 | 12/2007 | Urquhart et al. | |
| 7,497,863 B2 * | 3/2009 | Solar et al. ................... 606/130 |
| 7,507,242 B2 | 3/2009 | Triplett et al. | |
| 8,137,267 B2 * | 3/2012 | Shelton et al. ................ 600/203 |
| 8,226,553 B2 * | 7/2012 | Shelton et al. ................ 600/208 |
| 8,376,938 B2 * | 2/2013 | Morgan et al. ............... 600/204 |
| 8,425,410 B2 * | 4/2013 | Murray et al. ................ 600/203 |
| 8,430,811 B2 * | 4/2013 | Hess et al. .................... 600/203 |

(Continued)

*Primary Examiner* — Ellen C Hammond
*Assistant Examiner* — Stuart S Bray
(74) *Attorney, Agent, or Firm* — Fred C. Hernandez; Mintz Levin Cohn Ferris Glovsky and Popeo, P.C.

(57) ABSTRACT

This disclosure is directed to minimally-invasive devices, methods and systems used through small access portals to minimize trauma to structures adjacent the treatment site. The access device includes a guide frame and a cannula support washer movebly coupled to the guide frame. The washer has a cannula port aperture extending therethrough and a surface geometry complementary to the surface geometry of the guide frame. The complementary surface geometries limit movement of the cannula port aperture to arcuate movement along a surface segment of a sphere.

14 Claims, 5 Drawing Sheets

(56) References Cited

U.S. PATENT DOCUMENTS

| | | |
|---|---|---|
| 8,435,174 B2 * | 5/2013 | Cropper et al. .............. 600/203 |
| 8,475,362 B2 * | 7/2013 | Sohn et al. .................. 600/114 |
| 2003/0055436 A1 * | 3/2003 | Daum et al. ................. 606/130 |
| 2003/0187351 A1 | 10/2003 | Franck et al. |
| 2004/0167543 A1 * | 8/2004 | Mazzocchi et al. .......... 606/130 |
| 2005/0033315 A1 * | 2/2005 | Hankins ....................... 606/129 |
| 2005/0165281 A1 * | 7/2005 | Ravikumar et al. .......... 600/204 |
| 2005/0215863 A1 * | 9/2005 | Ravikumar et al. .......... 600/204 |
| 2006/0122627 A1 * | 6/2006 | Miller et al. ................. 606/129 |
| 2006/0122628 A1 * | 6/2006 | Solar et al. .................. 606/130 |
| 2006/0122629 A1 * | 6/2006 | Skakoon ...................... 606/130 |
| 2006/0192319 A1 * | 8/2006 | Solar .......................... 264/271.1 |
| 2006/0195112 A1 * | 8/2006 | Ek ................................. 606/86 |
| 2006/0195119 A1 * | 8/2006 | Mazzocchi et al. ........... 606/129 |
| 2007/0016199 A1 | 1/2007 | Boehm, Jr. et al. |
| 2007/0016296 A1 | 1/2007 | Triplett et al. |
| 2007/0191867 A1 * | 8/2007 | Mazzocchi et al. ........... 606/129 |
| 2008/0146881 A1 * | 6/2008 | Alimi et al. ................... 600/204 |
| 2009/0024141 A1 * | 1/2009 | Stahler et al. ................ 606/130 |
| 2009/0118743 A1 * | 5/2009 | Solar et al. ................... 606/130 |
| 2009/0270685 A1 * | 10/2009 | Moreno et al. ............... 600/203 |
| 2009/0270686 A1 * | 10/2009 | Duke et al. ................... 600/203 |
| 2010/0228091 A1 * | 9/2010 | Widenhouse et al. ........ 600/203 |
| 2010/0228092 A1 * | 9/2010 | Ortiz et al. ................... 600/204 |
| 2010/0249518 A1 * | 9/2010 | Battles ......................... 600/204 |
| 2011/0124967 A1 * | 5/2011 | Morgan et al. ............... 600/204 |
| 2011/0160538 A1 * | 6/2011 | Ravikumar et al. .......... 600/204 |
| 2011/0201891 A1 * | 8/2011 | Smith et al. .................. 600/203 |
| 2012/0101341 A1 * | 4/2012 | Malandain et al. ........... 600/204 |

* cited by examiner

ARCUATE SURGICAL GUIDANCE SYSTEM AND METHODS

REFERENCE TO PRIORITY DOCUMENT

This application claims priority of U.S. Provisional Patent Application Ser. 61/229,179, entitled "Arcuate Surgical Guidance System and Methods" by Marino, et. al., filed Jul. 28, 2009. Priority of the filing date of Jul. 28, 2009 is hereby claimed, and the disclosure of the Provisional Patent Application is hereby incorporated by reference.

BACKGROUND

Minimally-invasive techniques have been developed that prevent the need for excessive tissue dissection in and around target structures. However the manipulation of percutaneous surgical systems near critical or more delicate structures can cause unwanted damage.

SUMMARY

The subject matter described herein provides many advantages. More details of the devices, systems and methods are set forth in the accompanying drawings and the description below. Other features and advantages will be apparent from the description and drawings.

The minimally-invasive surgical systems described herein can be used for a variety of interventions within an organ, tissue mass, body cavity, joint or other soft tissue structure or osseous structure minimizing cannula manipulative trauma to structures immediately adjacent thereto. It should be appreciated that the anatomic region within which the system can be used is not limiting.

In an embodiment, described herein is a guidance system used to prevent manipulative trauma to tissue structures near a target treatment area accessed by a cannula. The guidance system includes an upper guide element having a first opening extending through the upper guide element; a lower guide element coupled to the upper guide element such that a space is formed between the upper and lower guide elements. The lower guide element has a second opening having a shape complementary to the first opening, and the first and second openings align to form an elongate channel. The system also includes an alignment washer having a central port extending through the alignment washer that is accessible via the first opening, the alignment washer slidably disposed within the space between the upper guide element and the lower guide element. The upper guide element, lower guide element and alignment washer each have a geometry that conforms to a segment of a sphere.

The space can have a width at least as wide as a thickness of the alignment washer. The guidance system can further include a locking element coupled to the upper guide element and lower guide element such that the width of the space between the upper guide element and lower guide element is reduced to fix the orientation of the alignment washer within the space. The guidance system can further include a cannula extending through the central port. The cannula and the alignment washer can be configured to coordinately move within the elongate channel in a variety of axes along the segment of the sphere. A portion of the cannula can extend to the target treatment area. The target treatment area can be distal to a center of the sphere. The portion of the cannula extending distal to the center of the sphere can be configured to undergo distal arcuate movement. A portion of the cannula encircled by the central port can be configured to undergo proximal arcuate movement. The proximal arcuate movement and distal arcuate movement can be complementary. The movement of a portion of the cannula at the center of the sphere can be minimized.

In an embodiment, disclosed herein is a method of minimally-invasive tissue access including inserting an intracorporeal instrument through a cannula guide device including a guide frame and a cannula support washer moveably coupled within the guide frame and having a cannula port extending through the cannula support washer. The guide frame and the cannula support washer together have a shape that is a surface segment of a sphere. The method also includes telescopically extending the instrument through the cannula port of the cannula support washer until a distal end of the instrument is adjacent an anatomic structure. The method also includes moving a proximal end of the instrument within the cannula port in the cannula support washer within the guide frame along the surface segment of the sphere while the distal end of the instrument pivots about a fixed point at a center of the sphere.

In another embodiment, disclosed herein is a minimally-invasive tissue access device including a guide frame having a first surface geometry; and a cannula support washer moveably coupled to the guide frame and having a cannula port aperture extending through the washer. The cannula support washer has a second surface geometry complementary to the first surface geometry. The complementary surface geometries of the guide frame and the cannula support washer limit movement of the cannula port aperture to arcuate movement along a surface segment of a sphere.

The cannula port aperture can be configured to receive a cannula extending through the aperture to a distance from the cannula port aperture that approaches a center of the sphere. Arcuate movement of the cannula support washer within the guide frame can limit movement of the cannula at the center of the sphere to a pivot point and can allow for translation of the cannula along a radial axis of the sphere. The distance can be the radial distance of the sphere between the pivot point of the cannula extending through the cannula port aperture and the cannula support washer aperture.

Other features and advantages should be apparent from the following description of various embodiments, which illustrate, by way of example, the principles of the invention.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

DETAILED DESCRIPTION

In percutaneous surgical procedures in which a small access channel and cannula is placed into or through a specific anatomic region, limited surgical dissection or manipulation can be desirable. As an example, it can be desirable to limit contact with the periannular structures of the lumbar disc, such as exiting spinal nerves within the foramen or the psoas muscle during surgical procedures intended for structures of the distal regions such as within the intervertebral disc space. In order to conduct surgical procedures in these distal regions some degree of manipulation is necessary.

Described herein are devices, systems and methods for a variety of surgical interventions within an organ, tissue mass, body cavity, joint or other soft tissue structure or osseous structure that minimize cannula manipulative trauma to structures immediately adjacent to the structures being treated. In particular, disclosed herein is an instrument guidance system that constrains an access cannula and associated instrumentation within delicate anatomic regions where minimal manipulation is desired and allows for some distal arcuate movements within the distal surgical field. The instrument guidance system described herein allows for proximal and distal arcuate movements and maintains a fixed pivoting region characterized by minimal movement.

It should be appreciated that although the present disclosure generally relates to spinal surgery, particularly to minimally-invasive, low-trauma surgical methods and improved access for associated interventions (e.g. disc excision and endplate decortication), the anatomic region within which the system is used can vary and is not limiting.

Figures 1A, 1B:
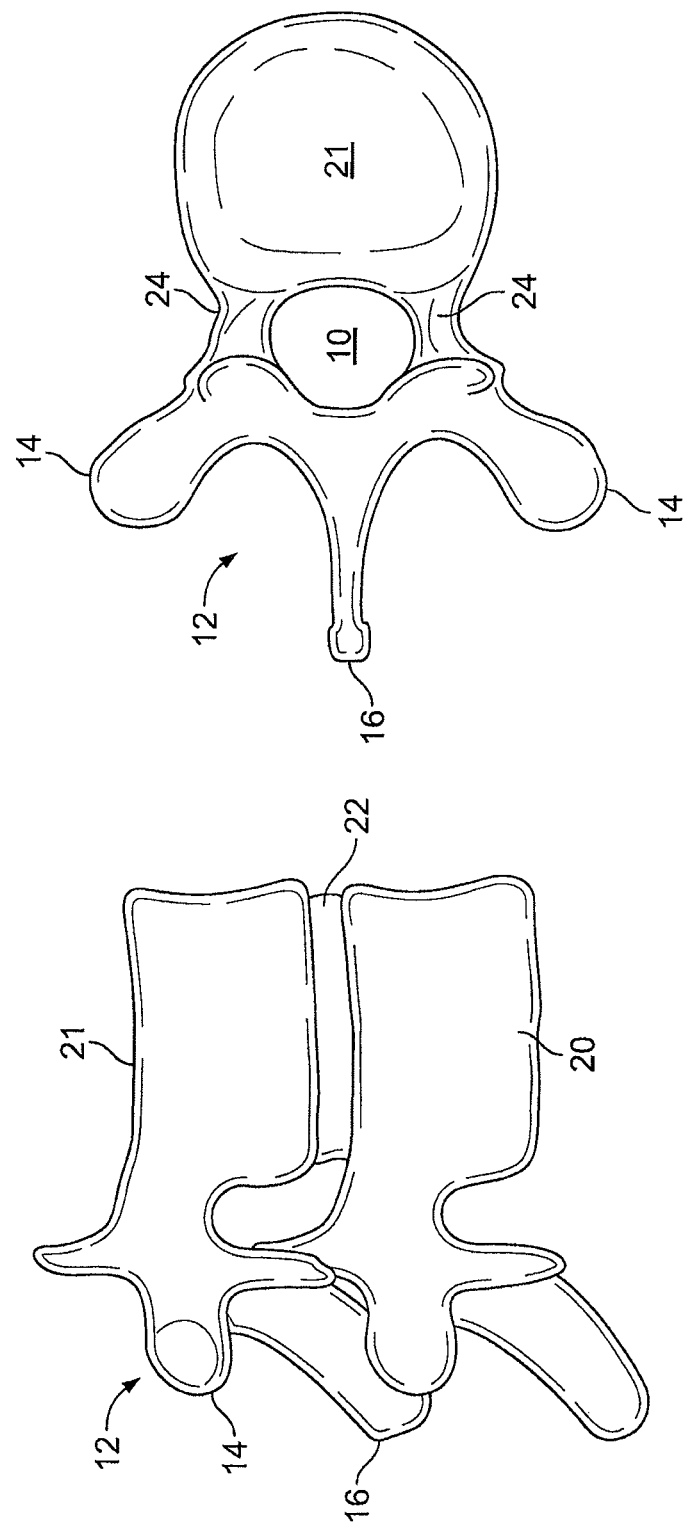
FIG. 1A is a simplified sagittal view of a vertebral pair.
FIG. 1B is a simplified, transverse plane view of a vertebra.

FIG. 1A is a simplified sagittal view of a vertebrae pair 20, 21. FIG. 1B is a simplified, transverse plane view of the vertebrae 21 of the vertebrae pair shown in FIG. 1A. Each vertebra 20, 21 includes lamina 12, transverse processes 14, a spinous process 16, central canal 10, and pedicles 24. A disc 22 comprised of an annulus and disc nucleus (not shown) is located between the vertebrae pair 20, 21. The spinal cord (not shown) passes through the central canal 10. Small nerve roots branch off from the spinal cord through spaces or neuroforamen of each vertebra. Due to disc degeneration, expulsion, annulus tears, or other conditions, the spinal cord or other nervous structures can become compressed causing patient discomfort.

It can be desirable to modify or fix the spatial relationship between the vertebrae pair 20, 21 and access the disc space or superior vertebra in order to decompress nerves, for example, to remove herniated or prolapsed discs. For example, access to the disc space 22 or superior vertebra 21 can be achieved via a channel(s) formed percutaneously in an inferior vertebra pedicle 24, such as one immediately inferior to the disc space or vertebra to be entered. The channel(s) can be used for a number of procedures such as disc resection, excision, endplate decortication, vertebral reduction or compression, delivery of material, pedicle screw fixation, etc.

Figure 2A:
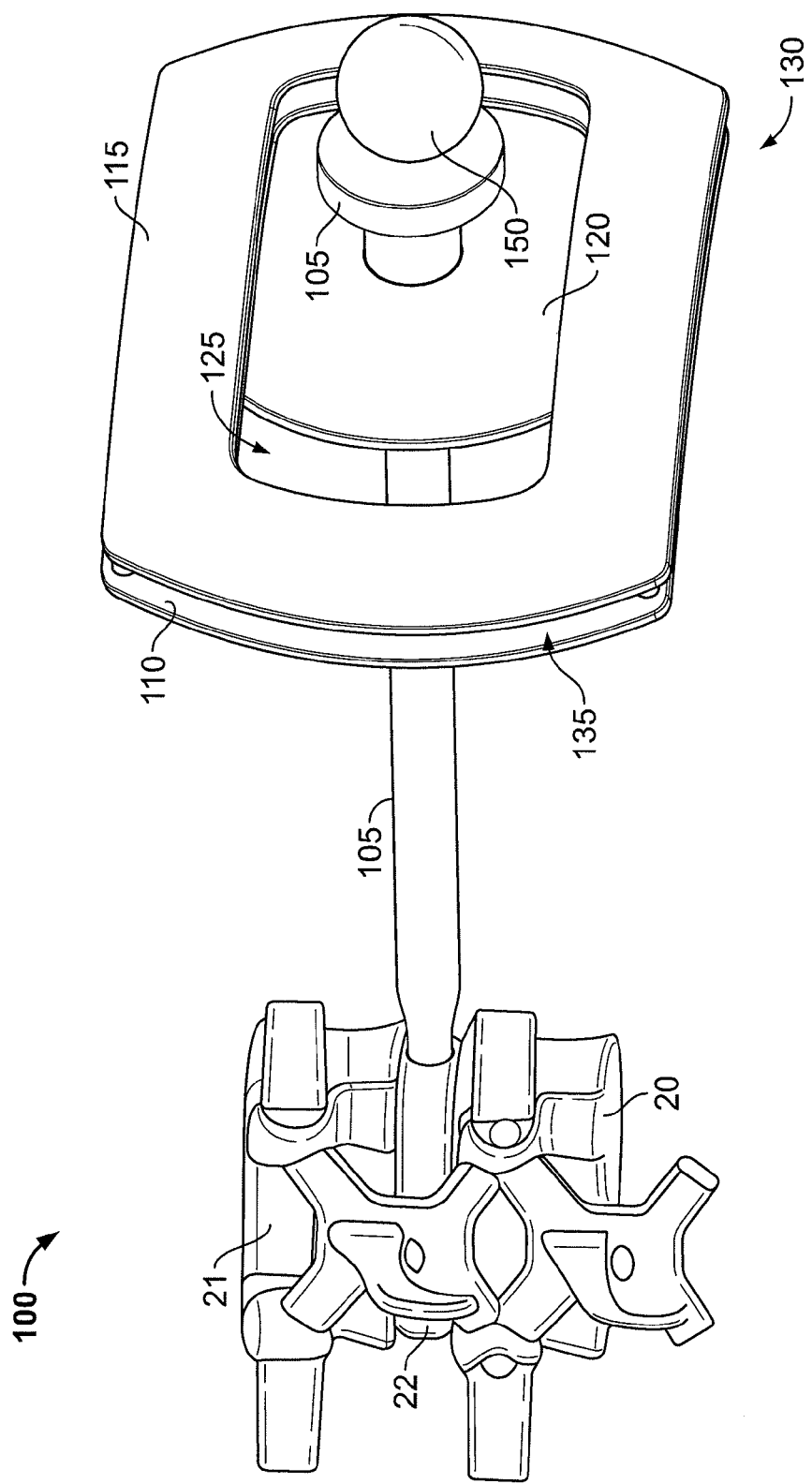
FIG. 2A is a simplified, perspective view of a vertebral pair including an embodiment of a surgical guidance system.
Figure 2B:
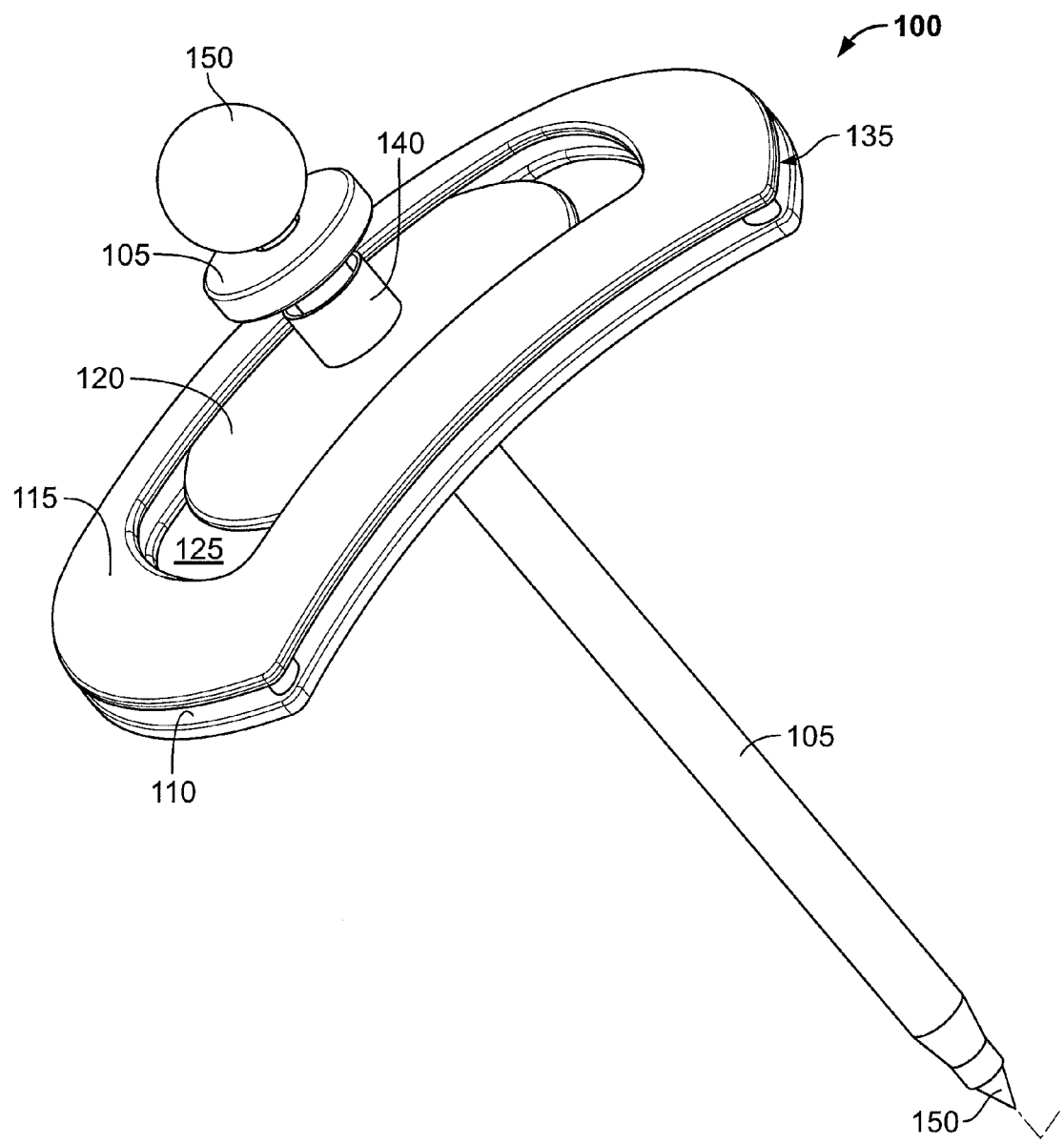
FIG. 2B is a perspective view of the surgical guidance system of FIG. 2A.

In an embodiment as shown in FIGS. 2A-2B, the instrument guidance system 100 can include a lower guide element 110, upper guide element 115, and an alignment washer 120 having a central port 140 through which a cannula 105 can be inserted. The lower guide element 110, upper guide element 115 and the alignment washer 120 each can have a complementary geometry that conforms to a segment of a sphere. The two guide elements 110, 115 can couple together with the alignment washer 120 disposed in a space 135 between them forming an arcuate guide 130 for a cannula 105. The space 135 between the guide elements 110, 115 can be at least as wide as the alignment washer 120 is thick such, that the washer 120 can be manipulated in sliding fashion between the upper and lower guide elements 110, 115.

Each of the guide elements 110, 115 can have an opening such that when the guide elements 110, 115 couple together the openings align and an elongate channel 125 extends therethrough. The alignment washer 120 sandwiched between the guide elements 110, 115 can span this elongate channel 125 such that at least a portion of the washer 120 remains sandwiched between the guide elements 110, 115 regardless of the positioning of the cannula 105 within the elongate channel 125. As mentioned above, the alignment washer 120 includes a central port 140 through which a cannula 105 can be inserted such that when the cannula 105 extends through the port 140 of the washer 120 it also extends through the elongate channel 125. The channel 125 allows for the cannula 105 and the washer 120 to coordinately move in a variety of axes along the surface of the sphere. The geometry and size of the openings and thus, the elongate channel 125 can vary. For example, the channel 125 can have a rectangular, square, circular, oblong, arcuate or other geometry. Movement of the cannula 105 within the channel 125 can be limited by the size and shape of the channel 125.

As mentioned above, the lower guide element 110, upper guide element 115 and the alignment washer 120 each can have a complementary geometry that conforms to a segment of a sphere. The combination of these elements provides an overall geometry to the arcuate guide 130 that conforms to that same segment of a sphere. The geometry of the arcuate guide 130 can vary. The arcuate geometry can be for a generally fixed radial distance. Depending on the anatomic location to be treated or accessed, the geometry and dimensions can vary. For example, the guide 130 can have variable geometries and sizes as can the length of the cannula 105 such that the guidance system 100 can correspond with the radial distance from the anticipated guide position to the anatomic structure within which it is desired that the cannula pivot. Multiple arcuate guides 130, such as a set or kit of guides, with varying radial geometries can be provided for corresponding radial distances. A surgeon can select an appropriate pivot point at a fixed distance from the anticipated location of the arcuate guide 130.

The instrument guidance system 100 can also include a locking element (not shown). Once the cannula 105 extending through the central port 140 is properly positioned in a particular axis along the segment of the sphere it can be desirable to fix the orientation of the cannula 105 within the arcuate guide 130. Similarly, a locking element can be used to fix the cannula 105 to the port 140 through which it passes. The locking element(s) can be of a variety of mechanisms including screws, clamps, friction locks, cam driven locks or other mechanisms as is known in the art. In an embodiment, the locking element clamps the lower and upper guide elements 110, 115 such that the space 135 between them is minimized and the washer 120 is fixed in place between the lower and upper guide elements 110, 115.

Various tools and instruments 150 can be inserted through the cannula 105 and employed via the instrument guidance system 100 to perform procedures. In the example of spinal surgery, it might be desirable to remove disc material, osteophytes or other structures that might be impinging on the nerve root(s), including herniated or prolapsed disc material. Other procedures that can be performed in addition to discectomy, include functional placement devices such as nucleoplasty or arthroplasty devices, endplate "decortication" instruments, annular closure or repair instruments and implants, fusion instrumentation and implants or intervertebral disc arthrodesis devices, fracture reduction devices, bone cyst therapy, intervertebral distraction devices, spacers or cages. Implantation of therapeutic materials such as bone growth materials, nuclear replacement material, bone granules, powdered material, and bone grafting material (autogenous, allogeneic, xenograph, or synthetic) as well as any osteoconductive and/or proliferative material, are also considered herein. More specifically, therapeutic bone growth materials such as osteogenic proteins or growth factors including osteoprogenic factor 1, BMP-7, and bone morphogenetic proteins such as BMP-2.

Figure 3:
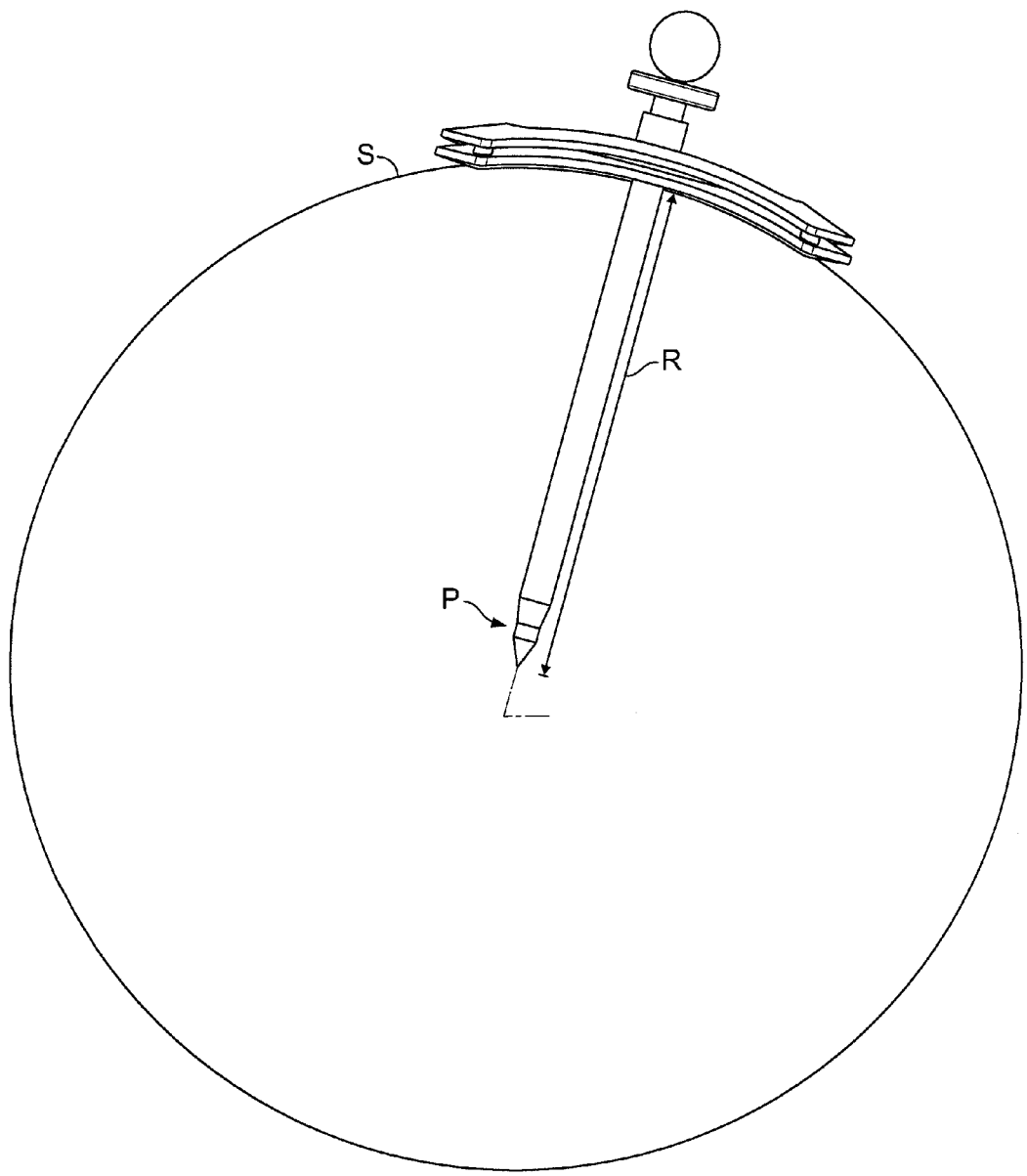
FIG. 3 is a schematic of the surgical guidance system positioned along a surface of a sphere.

As shown in FIG. 3, the arcuate guide 130 has a predetermined radius of curvature R whereby all radii, having radius of curvature R, extending from the arcuate guide 130 will intersect at a common point P, which is the center of an imaginary sphere S. A medical instrument 150 inserted through the cannula 105 disposed anywhere on the arc will dissect with common point P. The arcuate guide 130 is a segment of a sphere and the cannula 105 can be manipulated within this spherical segment by virtue of its movement with the alignment washer 120 within the elongate channel 125. The target work space (e.g. annulus) can be located at the common point P or just distal to the common point P.

Figure 4:
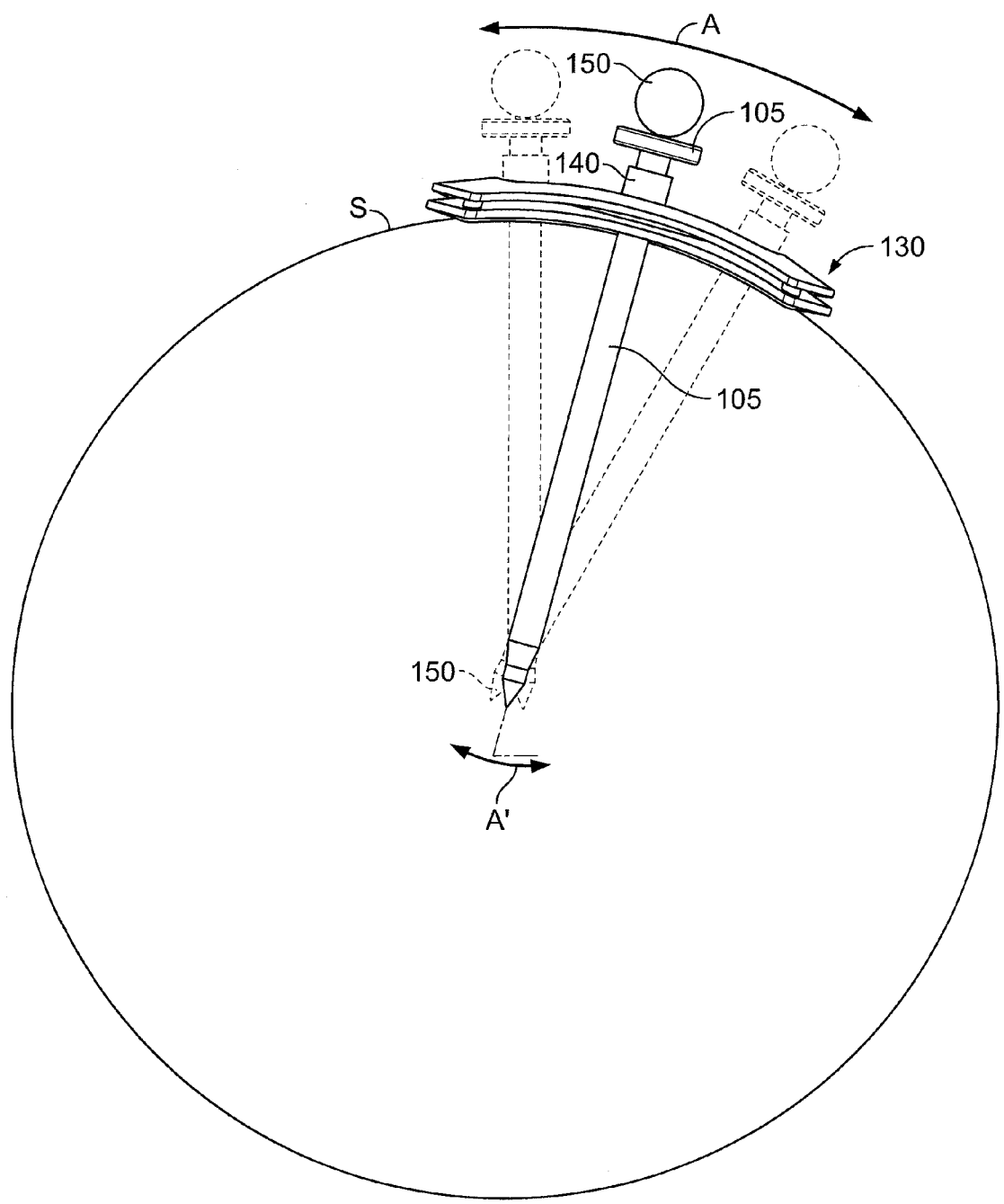
FIG. 4 is a close-up view of the surgical guidance system being actuated along a surface segment of a sphere.

As shown in FIG. 4, a distal arcuate movement (arrow A') near the target work space can occur that is complementary to the proximal arcuate movement (arrow A) within the arcuate guide 130. The distal arcuate movement allows for instrumentation 150 inserted through the cannula 105 to be used to perform surgical procedures, such as within the annulus. The common point P of the cannula 105 (and, in turn, any instrumentation 150 inserted through the cannula 105) undergoes minimal movement therein preventing tissue damage of the tissues surrounding a structure targeted for treatment.

The special orientation of the instrument guidance system 100 with respect to the patient can also be adjusted. In an embodiment, the instrument guidance system 100 is attached to an operating table by a table clamp and an adjustable bracing system that is adjustable along a variety of axes.

While this specification contains many specifics, these should not be construed as limitations on the scope of the claims or of what can be claimed, but rather as descriptions of features specific to particular embodiments. For example, although some of the present disclosure is presented in terms of spinal surgery, this is not intended to be limiting. The devices, systems and methods described herein can be used in a variety of anatomic locations where it would be desirable for cannula manipulation trauma to be minimized.

Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method of minimally-invasive tissue access, comprising:
    inserting an intracorporeal instrument through a cannula guide device, the cannula guide device comprising:
        a guide frame comprising a lower guide element having a convex upper surface and an upper guide element having a concave lower surface; and
        a cannula support washer moveably coupled within the guide frame between the upper guide element and lower guide element, the washer having a concave lower surface in contact with the convex upper surface of the lower guide element and having a cannula port extending through the cannula support washer wherein the lower guide element, the upper guide element and the cannula support washer each have a complementary geometry that conforms to a surface segment of a sphere;
    telescopically extending the instrument through the cannula port of the cannula support washer until a distal end of the instrument is positioned intracorporeally and adjacent an anatomic structure; and
    moving a proximal end of the instrument within the cannula port in the cannula support washer within the guide frame along the convex upper surface around a fixed point located intracorporeally near the distal end of the instrument.

2. The method of claim 1, wherein the upper guide element of the guide frame further comprises:
    a first opening extending through the upper guide element and the lower guide element is coupled to the upper guide element such that a space is formed between the upper and lower guide elements, and
    wherein the lower guide element has a second opening having a shape complementary to the first opening, and the first and second openings align to form an elongate channel.

3. The method of claim 2, wherein the central port extending through the cannula support washer is accessible via the first opening.

4. The method of claim 2, wherein the cannula support washer is slidably disposed within the space between the upper guide element and the lower guide element.

5. The method of claim 4, wherein the space has a width at least as wide as a thickness of the cannula support washer.

6. The method of claim 5, further comprising fixing the orientation of the cannula support washer within the space by reducing the width of the space.

7. The method of claim 1, wherein moving a proximal end of the instrument further comprises moving a portion of the instrument encircled by the cannula port along a proximal arcuate path constrained to the convex upper surface.

8. The method of claim 7, wherein moving a proximal end of the instrument further comprises moving the distal end of the instrument along a distal arcuate path.

9. The method of claim 8, wherein the proximal arcuate path and the distal arcuate path are complementary.

10. The method of claim 2, wherein moving a proximal end of the instrument comprises coordinately moving the instrument and the cannula support washer within the elongate channel.

11. The method of claim 1, wherein the distal end of the instrument extends to the anatomic structure.

12. The method of claim 1, wherein the anatomic structure is located distal to the fixed point.

13. The method of claim 1, further comprising limiting movement of the instrument to pivoting movements about the fixed point and axial translating movements along a radial axis.

14. The method of claim 1, wherein the intracorporeal instrument is a cannula.

\* \* \* \* \*